United States Patent [19]

Kuehn

[11] Patent Number: 5,201,865
[45] Date of Patent: Apr. 13, 1993

[54] MEDICAL LEAD IMPEDANCE MEASUREMENT SYSTEM

[75] Inventor: Kevin P. Kuehn, White Bear Lake, Minn.

[73] Assignee: Medtronic, Inc., Minneapolis, Minn.

[21] Appl. No.: 783,651

[22] Filed: Oct. 28, 1991

[51] Int. Cl.[5] .............................................. A61N 1/08
[52] U.S. Cl. .............................................. 128/419 PT
[58] Field of Search ....... 128/419 PT, 419 P, 419 PL, 128/419 D

[56] References Cited

U.S. PATENT DOCUMENTS

| | | | |
|---|---|---|---|
| 4,140,131 | 2/1979 | Dutcher et al. | 128/419 PT |
| 4,245,643 | 1/1981 | Benzing, III et al. | 128/419 PT |
| 4,337,776 | 7/1982 | Daly et al. | 128/419 PT |
| 4,406,286 | 9/1983 | Stein | 128/419 PG |
| 4,476,868 | 10/1984 | Thompson | 128/419 PG |
| 4,548,209 | 10/1985 | Wieders et al. | 128/419 D |
| 4,595,009 | 6/1986 | Leinders | 128/419 D |
| 4,630,615 | 12/1986 | Yomtov | 128/419 C X |
| 4,899,750 | 2/1990 | Ekwall | 128/419 PG |
| 4,949,720 | 8/1990 | Thompson | 128/419 P |
| 4,958,632 | 9/1990 | Duggan | 128/419 PG |
| 5,003,975 | 4/1991 | Hafelfinger et al. | 128/419 PG |

Primary Examiner—Lee S. Cohen
Assistant Examiner—Jeffrey R. Jastrzab
Attorney, Agent, or Firm—Reed A. Duthler; Harold R. Patton

[57] ABSTRACT

A method and apparatus for measuring lead impedance during preselected test mode operation of an implantable body tissue stimulator. The analysis circuitry is periodically triggered into operation, such as on each reprogramming by the physician or periodically as a function of elapsed time or number of stimulation events counted from the preceding measurement. The actual lead impedance, measured from the output circuit from the body tissue-stimulator pulse generator, and taking into account impedance of the interconnection between the lead connector pin and the pulse generator connector block, the lead electrical conductor and its connections with the electrode and the connector pin and the electrode-tissue interface, is calculated as a function of the ratio of the elapsed times that it takes to discharge a capacitor from a first reference voltage to a second reference voltage through a precision resistor and through the lead impedance itself The calculated lead impedance may be stored in memory with a suitable time tag, employed to automatically effect a change in operating modes or change a lead and electrode selection, if measured lead impedance falls outside normal high and low impedance boundary values. In the pacing context, calculated lead impedance may be employed to adjust sense amplifier sensitivity and pacing output pulse parameters. The method and apparatus may also be employed to calculate cardioversion/defibrillation lead impedance through selective partial discharge of high voltage output capacitors.

3 Claims, 2 Drawing Sheets

MEDICAL LEAD IMPEDANCE MEASUREMENT SYSTEM

BACKGROUND OF THE INVENTION

1. Field of the Invention

This invention pertains generally to the field of implantable body tissue stimulators, e.g., cardiac single chamber and dual chamber pacemakers and cardioverters, and more specifically to a method and apparatus for monitoring associated implanted lead and electrode impedance characteristics for analysis and modification of lead selection, operating mode and output pulse parameters.

2. Description of the Prior Art

Implantable body tissue stimulators usually include an electrode in contact with tissue to be stimulated mounted on a lead or housing containing an electrical conductor to be connected between the electrode and a source of stimulating energy. Usually the stimulating energy source is a fully implanted pulse generator which provides a capacitive discharge output pulse or shock to the electrode through the lead. Such pulse generators and stimulators include cardiac pacemakers, nerve and muscle stimulators and cardioverters, including combined pacemaker-cardioverter-defibrillator devices. Moreover, such devices usually include sense amplifiers coupled to the leads and electrodes specifically designed to sense spontaneous electrical activity of skeletal muscle and heart tissue. The integrity of the lead and electrode as measured by its impedance can critically affect both stimulation and sensing performance.

The technology of cardiac pacemakers implantable nerve stimulators and pacemakers-cardioverters-defibrillators has developed a high level of sophistication of system performance. The current generation of cardiac pacemakers and pacemaker-cardioverter-defibrillators incorporates microprocessors and related circuitry to sense and stimulate heart activity under a variety of physiological conditions. These devices may be programmed to control the heart in correcting or compensating for various heart abnormalities which may be encountered in individual patients. A background description of modern cardiac pacemaker technology is set forth in U.S. Pat. No. 4,958,632, which patent is incorporated herein by reference. It is a primary goal of programmable, multiple-mode, demand-type, cardiac pacemakers to accomodate the changing requirements of a diseased or malfunctioning heart. For example, single chamber, fixed rate pacers have been used extensively in the past to correct bradycardia, or slow heart rates Demand pacing is employed to avoid competing rhythms in patients who have some cardiac activity. Dual chamber pacing is used to treat complete or intermittent heart block by maintaining atrio-ventricular (AV) synchrony. Various other parameters (such as rate, pulse amplitude or width, sensitivity, refractory, etc.) may also need to be altered from time to time to custom-fit the pacemaker to each patient.

Programmability has also been incorporated into pacemakers to select the type of electrodes implanted, either unipolar or bipolar. A unipolar lead is one in which stimulation occurs between the cathode tip electrode and the pacemaker case, or anode. A bipolar lead is one in which stimulation occurs between the cathode tip electrode and an anode, ring electrode spaced approximately one inch from the tip electrode. Physicians select one lead type over the other for a variety of reasons. A unipolar lead may be chosen due to its advantage of being physically smaller and more flexible and, therefore, easier to implant. Unipolar leads also have the advantage of being less vector sensitive for intrinsic complexes (particularly premature ventricular and atrial contractions) due to the larger dipole. On the other hand, bipolar leads provide superior noise immunity to myopotentials and electromagnetic interference. It is also known that bipolar leads eliminate pectoral muscle stimulation, however, there has also been an occasional report of diaphragmatic stimulation. Since these leads are inaccessible after implantation (except by surgical procedure), bipolar leads may advantageously be used in either unipolar or bipolar configurations through noninvasive reprogramming of the implanted pulse generator.

While electronic circuitry can be, and is, incorporated within the pacemaker itself for exercising or testing various circuit components (such as the status of battery power sources, and the effectiveness of various amplifiers, waveform shaping stages and the like), it is often more difficult to test the integrity of the leads and implanted electrodes to which the pacemaker is coupled in order to verify that such leads and electrodes can function to allow for the desired pacing operation.

At the implantation of electrode systems, minor damage is sometimes incurred which may affect the lead s electrical insulation. This type of damage may go undetected and be without present effect on the implanted system, but the condition may manifest itself after extended time in service. When a breakdown or significant degradation of the pacemaker lead insulation occurs, it can result in a loss of sensing of intrinsic cardiac events or a loss of capture due to a lessened amount of energy reaching the cardiac tissue. Based on the underlying rhythm of the patient, this may have serious or even disastrous results. The reduced output energy reaching the heart is due to partial energy being shunted to other areas through the insulation opening.

Other types of damage can also occur to a pacemaker lead at implantation or later. A fracture in a conductor coil can affect operation by reducing the energy output to the cardiac tissue by causing a substantial increase in the lead resistance to current flow. A partial fracture will cause a reduction in output energy, while a complete fracture will result in no energy reaching the heart due to an infinite resistance (open circuit) Another type of detectable error relates to the failure of the electrode tip to be in proper contact with the heart wall.

It has been routine to measure lead impedance or stimulation threshold at the time of implantation to permit optimizing the location of the pacing lead and to maximize longevity of the pacer. These acute measurements are made with an oscilloscope or, more frequently, with a special instrument called a pacing system analyzer or PSA.

Later, after the lead has "healed" into the heart tissue, the margin of capture and delivered energy are estimated by the physician. With the advent of output pulse programmable pacers, physicians have been able to adapt the pacer's output to the threshold requirements of the patient and thus prolong the longevity of the implanted device.

To assist the physician with followup care, modern pacers use internal circuitry to monitor the output pulse parameters and to telemeter this information to the physician via a programmer. This information is used in assesing the performance of the pacemaker and the associated lead.

A problem which is presented by this technology is a discrepancy between the measured values of lead current and delivered energy presented by the programmer, PSA and oscilloscope. These differences result primarily from different measurement methodologies.

Typically, prior art pacers place a series resistor in the output path of the lead current, as disclosed, for example, in U.S. Pat. No. 4,140,131. During the delivery of a pacing stimulus, the voltage drop across the resistor is measured and telemetered out. This technique requires the use of a high precision resistor to reduce measurement errors. It also introduces a component whose failure can lead to an undesirable "no output" condition. Also, such a system is wasteful of output energy because of the inclusion of the measuring resistor.

Particular methods and apparatus for scanning the implanted leads of a pacemaker system to determine lead impedance and to detect abnormalities which may signal degradation and impending failure of pacemaker leads are the subject of the above-referenced '632 patent and U.S. Pat. Nos. 4,949,720; 4,899,750, and 5,003,975, all incorporated herein by reference.

Briefly, the '750 patent discloses systems for measuring the output voltage drop delivered to the pacing lead during pacing and determining the lead impedance from that measurement. The thus-determined lead impedance is compared with a moving average of the measured parameter and any deviation from that average by more than a predetermined amount is considered an anomaly. Three such anomalies in succession result in an event being counted in a first event counter for future consideration by a doctor during a patient checkup or the like. The system also monitors sensed heart signals and counts as a notable event any deviations in slope of the heart signal by more than a predetermined amount. These latter events are counted in a second counter to provide information for future reference. Thus, the '750 patent system determines the integrity of the implanted leads and electrodes by making measurements during both the pacing and sensing time intervals of the pacemaker timing cycle.

The '632 patent discloses measuring lead impedance as a function of the time that it takes to recharge the discharged output capacitor to full voltage, and automatically switching pacing electrodes or modes of operation if the time is excessively long (excessively high impedance) or excessively short (exclusively low impedance) or upon loss of capture. The '975 patent discloses similar responses to excessive or insufficient lead impedances, using the technique of the '750 patent.

The '720 patent discloses a lead impedance measuring circuit including a large number (typically 200) of FET transistors operated in parallel to discharge a capacitor through the heart tissue. Pacer lead current is monitored by measuring the current through a small number (typically 2) of these transistors. The current monitoring function is performed by a current-to-voltage converter coupled to an analog-to-digital converter which may make one or more voltage measurements during the output pulse. The ability to time the measurement with respect to the leading and trailing eges of the output pulse provides flexibility to match the telemetered pacing current data with operating room measurements thus reducing the confusion that discrepancies can cause. Additionally, the voltage developed by the current-to-voltage converter may be applied through additional circuitry to the gates of the FETS to provide for a constant current output pulse.

The aforementioned '750, '975 and '720 patents employed a technique for the calculation of lead and lead electrode-tissue interface impedance through measurement of the initial and final voltages across a coupling capacitor when the lead system is paced with a fixed pulse width pacing pulse. The voltage measurement is then translated into a current based on the capacitance value on the pulse width. The lead impedance is then calculated as the average voltage divided by the average current, from which known switch impedances are subtracted. The methods illustrated by these patents have several error items which contribute to overall inaccuracy of as much as ±20% in the 100–1000 ohm load range. These error terms include the impedance approximation equation (which avoids the natural log function in order to save on software), capacitance tolerance, analog to digital conversion accuracy, sampled voltage gain stage accuracy, sample and hold leakdown, voltage reference drift and pulse width tolerances of the programmed pacing pulse and the pulse generator circuit timeout thereof.

In commonly assigned co-pending U.S. patent application Ser. No. 619,494 filed Nov. 29, 1990, in the names of Wayne et al it is proposed to calculate lead impedance from lead current computed by measuring output capacitor discharge time over a continued output capacitor discharge occurring from the trailing edge of the pacing pulse until a threshold (which is automatically set to reflect the voltage drop occurring during the preceding output pulse) is reached.

Measurement of the lead impedance (including the impedance contributions of the electrical feedthrough and connector block components, the electrical connection between the connector block components and the lead conductor terminal pin physically attached thereto at implant, the lead conductor itself and its interconnections with the connector pin and electrode and the electrode-tissue interface which, as described above, all may change over time for a number of reasons) in an implanted pacing system allows the user to determine changes in characteristics in the lead as well as the electrode-tissue interface trends over a period of chronic implant. In implantable pacemaker pulse generators, measurement of parameters which are used to calculate the impedance of the lead/heart system must be accomplished in an accurate and precise manner without the aid of external instruments.

Impedance measurement of lead and electrode systems in other tissue stimulation contexts, particularly in high energy cardioversion and defibrillation, has been addressed in only a limited fashion. In external cardioversion and defibrillation, it is known to measure impedance to make certain that good electrode contact with the patient s body exists before applying the shock Implantable cardioversion and defibrillation electrodes are also subject to fracture or shorting out, and it would be desirable to be able to periodically measure lead impedance in order to detect changes reflecting impending or actual failures.

SUMMARY OF THE INVENTION

It is therefore an object of the present invention to provide a method and apparatus for automatically measuring lead impedance in an implantable tissue stimulation system relatively efficiently and accurately with the introduction of a minimal number of simple components.

It is a further object of the present invention to provide a body tissue stimulator output circuit possessing the characteristics described above wherein the lead impedance may be accurately measured on at least a periodic basis and the resulting measured impedance value may be stored for providing impedance trend data over time and may be employed by the stimulator to automatically change its operating modes or parameters in a fashion as described above. In accordance with the present invention, more accurate impedance values may be derived and employed for such purposes.

The method and apparatus of the present invention may be accomplished in a body tissue stimulator and lead system of the type comprising a pulse generator for providing body tissue stimulating pulses, a body tissue contacting electrode from which body tissue stimulating pulses are emitted and a lead system for electrically coupling an output pulse circuit of said pulse generator with said electrode, wherein said pulse generator output pulse is effected by triggered discharge of an output capacitor through said lead and electrode for a preselected time to provide a capacitive discharge, output pulse of a preselected pulse width and having a leading edge and a trailing edge voltage amplitude wherein the improved method of measuring lead impedance comprises the steps of: charging the capacitor to a first reference voltage; discharging the capacitor into a precision resistor of known resistance value; measuring the voltage on the capacitor during its discharge; measuring the discharge time from commencement of discharge until a second reference voltage on said capacitor is measured; again charging said capacitor to said first reference voltage; discharging the capacitor through the lead and electrode while measuring the voltage thereon; measuring the discharge time from commencement of discharge until the voltage on the capacitor reaches the second reference value; and determining the impedance of the lead from the known impedance of the precision resistor and the first and second measured discharge times as a function of the ratio of the second discharge time to the first discharge time multiplied by the known impedance of the precision resistor.

Advantageously, a number of the measured second discharge times and calculated lead impedance values are stored in memory on a first in first out basis for subsequent telemetry out and analysis, or the data is stored in histogram bins in memory for subsequent read out. In the pacing context, the measured lead impedance values may be compared to high and low impedance limit values, and the selection of the pacing leads and electrodes, the pacing energy delivered, and the sense amplifier characteristics may be automatically adjusted to account for deviant impedances. Moreover, the detection of a deviant lead impedance may trigger more frequent impedance measurement and updating of stored values and operating modes and parameters.

BRIEF DESCRIPTION OF THE DRAWINGS

The above and other objects, features and advantages of the present invention will be more apparent from the following description presented in conjunction with the accompanying drawings in which like reference numerals designate like parts throughout the figures thereof, and wherein.

DESCRIPTION OF THE PREFERRED EMBODIMENTS

Figure 1:
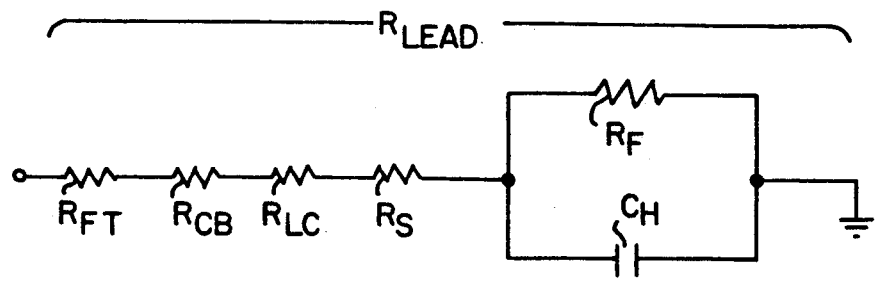
FIG. 1 is an illustrative schematic diagram of the effective electrode-tissue impedance, lead conductor impedance, connector block and connector pin impedance and feedthrough impedance as presented at the output of a pacing pulse generator.

As described above, the present invention may be employed in the measurement of both pacing and cardioversion lead and electrode impedances in single or dual chamber pacemakers as well as in pacemaker-cardioverter-defibrillators or in other body tissue stimulators. In the case of a cardiac pacemaker, the impedance testing routine may be entered into either periodically or by physician initiation with an external programmer by initiating a temporary asynchronous pacing mode of operation having a fixed escape interval wherein the output capacitor may be first discharged into a precision resistor load part way through the escape interval and the measurement of the time that it takes to discharge from VDD to VDD/2 can be conducted without having any effect on the patient Thereafter, at the end of the temporary escape interval (which is preferably set at a lower than normal test pacing rate, such as 60 beats per minute) the output capacitor may be discharged into the patient's pacing lead and heart in order to measure the time that it takes for the output capacitor to again discharge from VDD to VDD2. The two elapsed times may be stored in memory and processed to develop the current lead impedance value.

However, when testing the impedance of a cardio version/defibrillation electrode system, it is undesirable to shock the patient just to obtain the impedance value. Therefore, advantage is taken of the fact that periodically the function of the cardioverter/defibrillator output shock generating circuit is tested by the physician who initiates charging and discharging of the high voltage output capacitors into a test load in order to reform the capacitors which, by their nature, tend to lose their ability to charge if not charged and discharged periodically. In the course of that testing, the present invention may be practiced by measuring the time that it takes for the output capacitor voltage to decrease from a first reference value to a second reference value through the known impedance test load, where the first and second reference voltages are chosen to be at levels which are insufficient in and of themselves to cardiovert the patient. Then, the same procedure may be repeated by recharging the output capacitor and causing it to discharge from the first reference voltage to the second reference voltage through the electrode system and measuring the elapsed time in order to compare the two elapsed times and measure the cardioversion/defibrillation lead impedance.

Alternatively, the physician may elect to conduct a test of the system's ability to cardiovert the patient in an electrophysiologic study and, in the course of that procedure, the physician may first program the implanted device to charge up its high voltage output capacitors and discharge them into the test impedance, obtain the aforementioned elapsed time measurement, initiate stimulation to induce a tachyarrhythmia and program the device to both cardiovert or defibrillate the enduced tachyarrhythmia and to conduct the elapsed time measurement in accordance with the method of the present invention.

Turning now to FIG. 1, the overall impedance of a pacing or cardioversion lead and electrode system in contact with a patient's heart and as presented at the output circuit of either the pacemaker or the cardioverter/defibrillator shock generator is depicted as a series of resistances and capacitances. Since the output circuit in either case is viewing the remainder of the system through a feedthrough terminal, connector block connection, lead conductor system and electrode-tissue interface, each of those components may possess a discrete electrical series resistance. It will be understood that the normal resistances of the feedthrough, connector block and connector pin connection, lead conductor and its connections with the connector pin and electrode should remain relatively low and stable.

In pacing, employing relatively small pace/sense electrode surface areas, impedances at the electrode-tissue interface would be expected to range between 500 and 1000 ohms while total impedance of the remainder of the system, employing highly conductive alloys, would range between 10 and 20 ohms. Similarly, with cardioversion lead systems, the impedance of the electrical components would be expected to fall between 10 and 20 ohms, whereas the electrode-tissue interface impedance may range between 20 and 200 ohms. A relatively large surface area of the typical cardioversion/defibrillation electrode contributes to a lower electrode-tissue interface impedance.

FIG. 1 illustrates the effective series and parallel connected impedances of the components listed above where $R_{ft}$ represents the feedthrough resistance: $R_{cb}$ represents the connector block impedance: $R_{lc}$ represents the lead conductor and connection joint impedances of the lead conductor and its connections with the proximal conductor pin and the distal electrode; and wherein the electrode-tissue interface impedance which can be represented through an electrical impedance which comprises a series resistor $R_s$ in series electrically with a parallel combination of a Faraday resistor $R_f$ and a Helmholtz capacitor $C_h$. The entire series resistance of $R_{ft}$, $R_{cb}$, $R_{lc}$ and $R_s$ has a nominal value of about 10 to 200 ohms, the capacitor $C_h$ has a nominal value of about 5 to 50 microfarads, and the resistor $R_f$ has a nominal value of 2K to 100K ohms. These values apply for the impedance measured in gross terms across the output terminals of the pulse generator.

Figure 2:
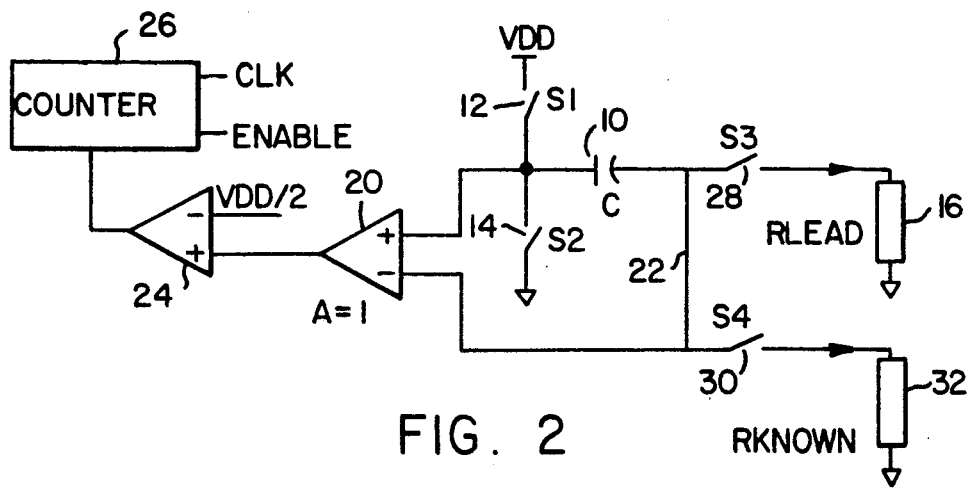
FIG. 2 is a circuit diagram of a preferred embodiment of the circuit for measuring the voltage drop across the output capacitor during the delivery of a test pulse into a reference load and into the pacing lead impedance and a timing circuitry for measuring the elapsed time that it takes the output capacitor voltage to drop by a predetermined amount.

Turning now to FIG. 2, it depicts in simplified form a typical pulse generator output circuit for either a pacemaker or a cardioverter wherein the output capacitor 10 of either such device is typically adapted to be charged to a programmed battery voltage VDD through a charging switch 12 and the lead system which is shown diagrammatically as $R_{lead}$ representing the impedance depicted in FIG. 1. At the appropriate time following the charging of capacitor 10, the switch 12 is opened and the switches 14 and 28 are closed in order to discharge capacitor 10 through $R_{lead}$ for the time duration or pulse width set by the closure of switch 14. The remaining elements of FIG. 2 may be incorporated into each embodiment and employed in the lead impedance measurement method and apparatus of the present invention. In the pacing context, the output circuit of FIG. 2 may take the form of the circuit depicted, for example, in U.S. Pat. No. 4,498,478 to Bourgeois or U.S. Pat. No. 4,476,868 to Thompson, or U.S. Pat. No. 4,406,286 to Stein, all incorporated by reference herein in their entirety. The switches 28 and 30 may take the form of transistor switches in a fashion taught by the above-incorporated '478, '868 and '286 patents.

Additional elements to the prior art output circuits by which the method and apparatus of the present invention may be implemented to include the first differential amplifier 20 coupled across the capacitor 10 by conductor 22, a second differential amplifier 24, the counter 26, the switches 28, 30, and the known precision resistor 32 all coupled as depicted in FIG. 2. The operation of the lead impedance measuring system is explained in conjunction with the waveform diagram of FIG. 3 and the flowchart diagram of FIG. 4.

Very generally, the lead impedance method follows the steps of charging the capacitor 10 to VDD, discharging the capacitor 10 through $R_{known}$ resistance 32, while at the same time enabling the counter 26 to start counting clock pulses, and to freeze the count in the counter 26 when the voltage across the capacitor 10 decreases to VDD/2, as determined by the first and second op amps 20 and 24 Thereafter, the process is repeated through the lead impedance presented to the output terminal of the pulse generator at switch 28, representing the discharge time of the capacitor 10 between the same starting and ending voltage. The first and second counts reflect the discharge time corresponding to a discrete number of clock pulse intervals denoted $t_{cap}$ and $t_{lead}$, respectively. $R_{known}$ remains constant and VDD should be a repeatable constant voltage for the two successive discharges of capacitor 10, the only variable in the time $t_{cap}$ from one pulse generator to another and over the life of the pulse generator in question should be the condition of the switches 14 and 30 and capacitor C. In practice, capacitor tolerances vary from one pulse generator to the next, and the repetitive cycling, particularly of high voltage electrolytic capacitors, causes the capacitance to change over time. Therefore, since the RC time constant of the capacitor 10 and precision resistor 32 may vary, the first discharge time is denoted $t_{cap}$, and it is measured and stored in memory at least on the first occasion that the lead impedance is calculated or, preferably, each time that it is calculated.

The relationship between the capacitance C of the capacitor 10 and the resistances $R_{known}$ of the precision resistor 32 and $R_{lead}$ for the combined lead impedance are expressed as follows:

$$VDD/2 = VDD(1-e^{-t/RC}),$$

$$C = t_{cap}/\ln(0.5)R_{known};$$

$$R_{known} = t_{cap}/\ln(0.5)C;$$

$$R_{lead} = t_{lead}/\ln(0.5)C; \text{ and}$$

$$C = t_{lead}/\ln(0.5)R_{lead}.$$

Since the resistance $R_{known}$ is known, it may be used as a constant, and the determination of the variable lead impedance $R_{lead}$ reduces to:

$$\frac{R_{lead} = -t_{lead}\ln(0.5)C}{R_{known} = t_{known}/\ln(0.5)C};$$

and results in $$R_{lead} = R_{known}(t_{lead}/t_{cap})$$

Known switch impedances for switches 14 and 28 may be subtracted or ignored if insignificant. This approach eliminates the need to use natural log functions or approximations thereof.

Figure 4:
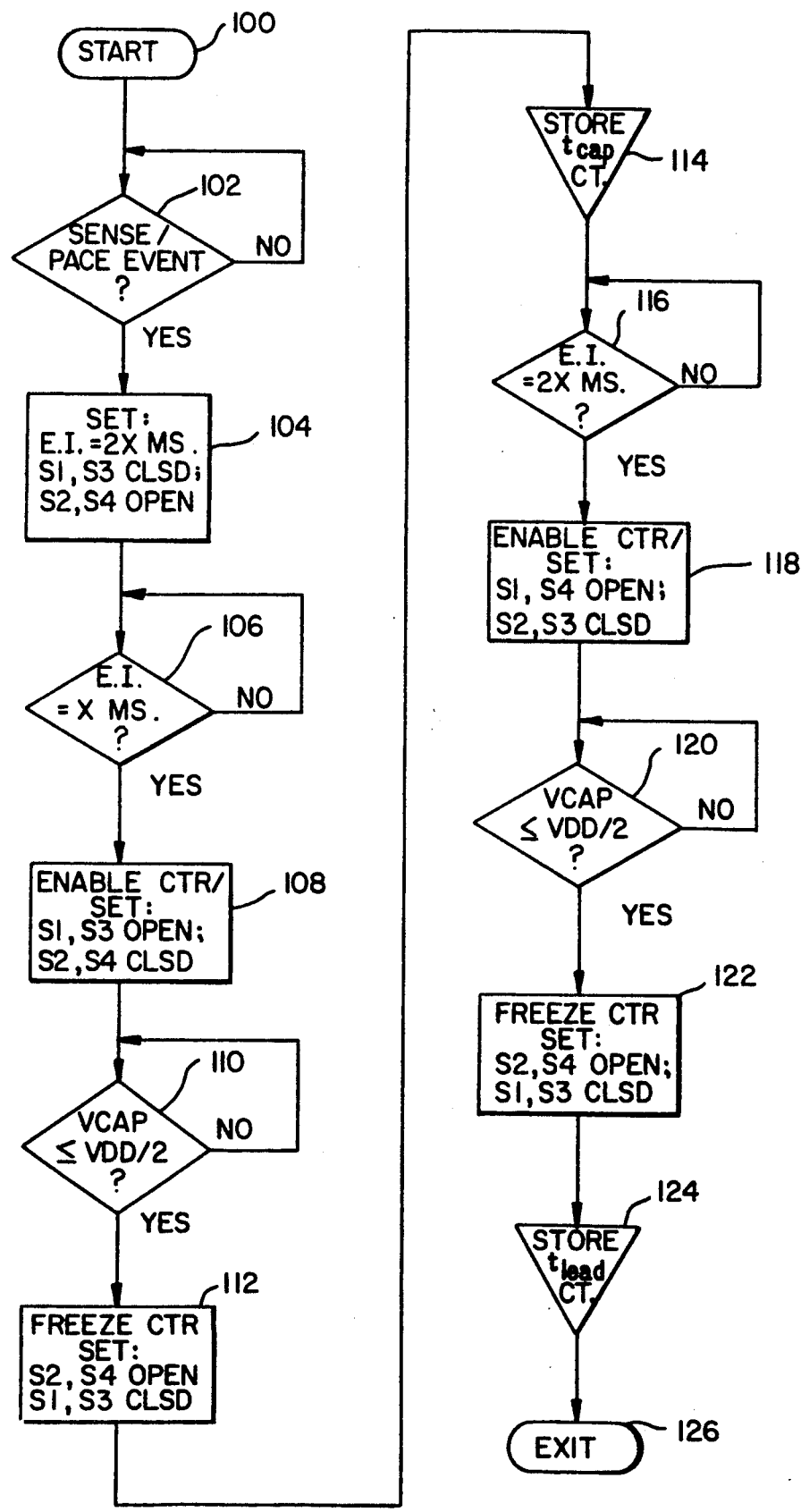
FIG. 4 is a flowchart diagram of the signal processing steps involved in the calculation of lead impedance in accordance with the present invention.

In the calculation of $R_{lead}$, the two counts are compared to one another and the ratio of the $t_{lead}$ to the $t_{cap}$ multiplied by the $R_{known}$ resistance yields the current $R_{lead}$ value in a manner to be described in conjunction with FIG. 4.

The above-described method may be employed also in the context of a cardioverter-defibrillator, where the capacitor 10 may take the form of the high voltage output capacitor and the voltage source VDD may take the form of the output of the DC-DC converter, as shown, for example in U.S. Pat. Nos. 4,595,009 and 4,548,209, filed in the names of Lebindors and Wielders. In that context, the $R_{lead}$ impedance constitutes the same impedance elements as depicted in FIG. 1 but in regard to a cardioversion/defibrillation lead system, rather than the pacing lead system previously described. Moreover, the fixed $R_{known}$ impedance element may take the form of the internal discharge resistor which is usually provided at 1-3K ohms. The switches 12, 14, 28 and 30 may constitute the high voltage silicone controlled switches and power FETs commonly employed in the output circuits of such devices.

Figure 3:
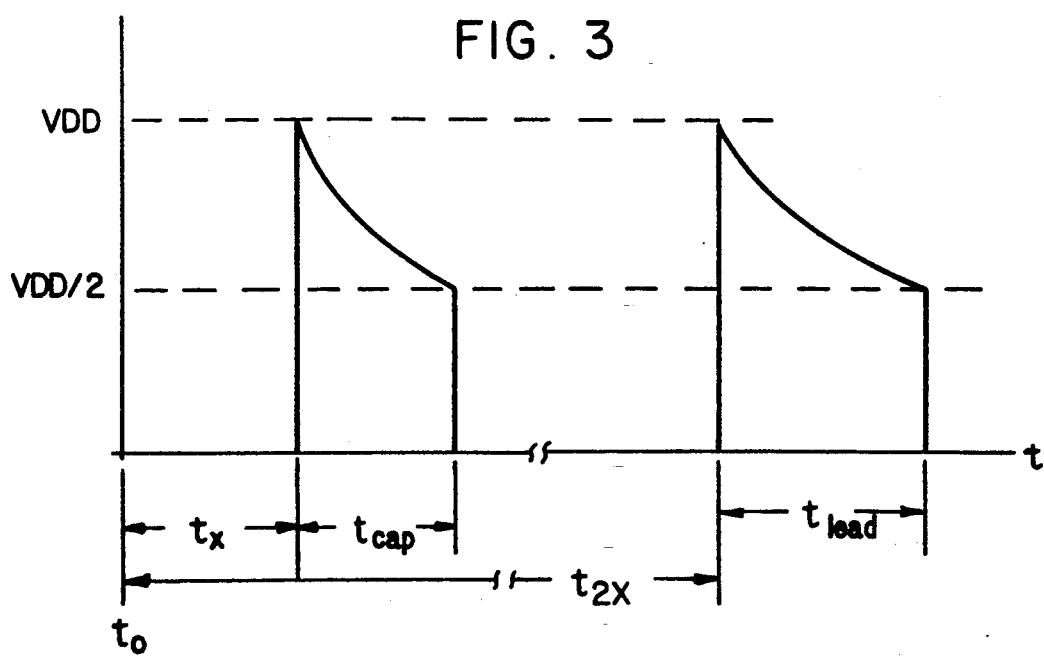
FIG. 3 is a waveform diagram illustrating the elapsed time out of the test load and pacing lead discharge of the output capacitor of FIG. 3.

Turning now to FIGS. 3 and 4, they describe the practice of a method of the present invention implemented in pacing context wherein it will be understood that the pacemaker is normally operating to repetitively timeout escape intervals which may be fixed at a previously programmed value or vary between preset upper and lower escape intervals in relation to a pacing rate control signal established by physiologic sensor, as is well known in the pacing art. At some point, either upon receipt of an external programmed-in command, the occurrence of a particular event or upon an internally timed-out self test command, the pacing logic or software commences a subroutine to initiate the successive measurement of the $t_{lead}$ and $t_{cap}$ time intervals Turning now to FIG. 3, the successive discharge of the capacitor 10 into the $R_{known}$ and $R_{lead}$ impedances is depicted along the time line T and in relation to the starting voltage VDD and ending voltage VDD/2. Once the impedance measurement algorithm is entered into, at start block 100 of FIG. 4, the pacing mode is changed to a temporary fixed rate mode at a preset escape interval for at least one escape interval denoted $t_{2x}$. Escape interval $t_{2x}$ may be selected to be in the range of 1,000 ms to allow for the successive charge and discharge of the capacitor 10 through both the $R_{known}$ and $R_{lead}$ impedances and still allow adequate time for the capacitor 10 to recharge. FIG. 3 illustrates the discharge of the capacitor 10 through the $R_{known}$ impedance at the end of the interval $t_x$ to develop the reference time period $t_{cap}$ and to subsequently allow the discharge of the capacitor 10 through the $R_{lead}$ impedance at the end of the escape interval $t_{2x}$ to develop the pulse width interval $t_{lead}$.

Turning now to FIG. 4, the testing subroutine starts at start block 100, which may precede the end of a current escape interval reflecting the receipt of a programmed-in command, for example. When the next pace or sensed event occurs, the escape interval is set to $2\times$ ms, switches 12 and 28 are closed and switches 14 and 30 are opened in block 104 to provide for the recharge of the capacitor 10 through the $R_{lead}$ impedance in the normal pacing fashion. During this time, the counter 26 is not enabled and as capacitor 10 charges up to VDD, its voltage is presented across the positive or negative input terminals of the unity gain differential to single-ended op amp 20, which in turn presents that voltage to the positive input terminal of differential amplifier 24. Differential amplifier 24 compares the voltage at its positive input terminal against a reference voltage, in this case one-half the VDD voltage or VDD/2, and provides an output signal at its output terminal whenever the presented voltage across the capacitor 10 exceeds the reference voltage VDD/2 less any offset voltages. The output of the differential amplifier 24 operates to freeze and transfer the contents of the counter 26 into memory when that presented voltage falls below the reference voltage VDD/2 as described hereinafter.

In block 108, and in reference to FIG. 3, at the end of the interval $t_x$ as timed out by decision block 108, the counter 26 is enabled, the switches 12 and 28 are opened and the switches 14 and 30 are closed. At that instant, the voltage VDD across the capacitor 10 is presented to the positive input terminal of the differential amplifier 24 and also begins to discharge through the $R_{known}$ impedance 32 in a fashion depicted by the capacitive discharge pulse having a width $t_{cap}$ depicted in FIG. 3. As long as the voltage on capacitor 10 is greater than VDD/2, counter 26 continues to count clock pulses. As soon as the voltage on the capacitor 10 falls below VDD/2, the output from the differential amplifier 24 switches from high to low, and the counter 26 receives a command to freeze the count, transfer it to a memory location or a separate register, and to disable itself. At the same time, this accumulated count may be reset to zero.

At the same time, the switches 14 and 30 are set open and switches 12 and 28 are set closed to terminate the discharge of the capacitor 10 and commence its recharge. The stored time interval $t_{cap}$ is held awaiting the measurement of the time $t_{lead}$, whereupon the mathematical comparison and multiplication steps take place.

Thereafter, the fixed escape interval $t_{2x}$ times out in block 116, and the counter 26 is again enabled in block 118. At the same time, the switches 12 and 30 are opened, and the switches 14 and 28 are closed. Thus, the discharge of the capacitor 10 through the $R_{lead}$ impedance commences at the end of the escape interval. Again, the voltage on the capacitor 10 is monitored by the differential amplifiers 20 and 24 and when it again falls below VDD/2, the contents of the counter 26 are frozen, transferred to a separate register and the counter cleared in blocks 122 and 124. At the same time, the switches 14 and 30 are opened, and the switches 12 and 28 are closed to commence the recharge. Once the count representing the time $t_{lead}$ is stored in block 124, the subroutine is exited in block 126, thus returning control of the pacing mode and rate to the normal operating pacing system.

Since the clock pulses have predetermined pulse widths, the accumulated counts transferred into memory at registers representing the time intervals $t_{cap}$ and $t_{lead}$ are fairly representative of the actual RC discharge times. Moreover, since the ratio of the two times are employed in the calculation of the current lead impedance, any voltage reference drift or other component value or operating parameter drift cancel one another out. Over the impedance range of 100 to 1000 ohms, the error tolerance is dependent upon the following factors:

Counter resolution vs. minimum decay time 30.5 uS/693 uS (100 Ohm, 10 uF) 4.4%
Counter resolution vs. nominal decay time 30.5 uS/3.53 mS (510 Ohm, 10 uF) 0.9%
Comparator offset: $<\pm 10$ mV ($<\pm 1\%$)
Op amp offset: $<\pm 10$ mV ($<\pm 1\%$)
Op amp gain accuracy: $\pm 1\%$
VDD/2 cap ratio accuracy: $\pm 0.1\%$
Pacing capacitor initial voltage $\pm 1\%$
Known load decay time $\pm 2.7\%$ (sum of errors in calculation of $t_{cap}$)

In theory, the measurement accuracy meets the goal of $\pm 5$–$10\%$ in the specified load range. The comparator and op amp errors are consistent between the known impedance pulse and the unknown impedance pulse effectively eliminating them from the overall summation of error terms.

In the cardioversion-defibrillation context, the method of FIG. 4 may be modified by eliminating the decision block 102 and setting an overall time interval in block 104 that may encompass 30 to 60 seconds to assure adequate charging to full program voltage. Although technically not an escape interval, the time-out of the set interval is necessary to assure that the output capacitor is fully charged. Alternately, if the cardioverter-defibrillator is provided with a circuit for monitoring the achievement of full charge on the output capacitor or capacitors, then the initial discharge through the $R_{known}$ impedance 32 and then the subsequent discharge through the $R_{lead}$ impedance 16 may take place upon confirmation of the capacitor output voltage VDD. In either case, the excessive charging and discharging of the capacitor 10 to develop the time intervals $t_{cap}$ and $t_{lead}$ occurs in the same fashion as described above.

In those instances where it is undesirable to discharge full output capacitor voltage through the $R_{lead}$ impedance on the patient, a smaller sub threshold voltage VDD may be selected or the reference voltage VDD/2 (i.e., 0.5 VDD) may be set at a higher value, such as 0.95 VDD.

In either case, the method and appartus of the present invention finds particular utility in the pacemaker-cardioverter-defibrillator context, inasmuch as the condition of the capacitors may change over time by virtue of their being repetitively subjected to high voltage charge and discharge cycles. In accordance with the present invention, changes in the applied voltage VDD, the capacitor 10 and the various switches are all taken into account and offset one another in the calculation.

Other modifications of the embodiments of the method and apparatus of the present invention will become readily apparent to those skilled in the art in light of the foregoing disclosure. Therefore the scope of the present invention should be interpreted from the following claims interpreted in light of the above-described preferred embodiments and other modifications and embodiments thereof.

What is claimed is:

1. A method of measuring the impedance of an implantable medical lead having an unknown impedance, comprising:
   a. Coupling said implantable lead to a pulse generator which includes an output capacitor and a precision resistor having a known resistance;
   b. Charging said output capacitor to a first predetermined voltage, discharging said output capacitor through said precision resistor and measuring the time interval during the discharge of said output capacitor from said first predetermined voltage to a second predetermined voltage;
   c. Charging said output capacitor to said first predetermined voltage, discharging said output capacitor through said lead and measuring the time interval during discharge of said output capacitor from said first predetermined voltage to said second predetermined voltage; and
   d. Determining the ratio of said measured time interval during discharge of said output capacitor through said lead impedance to said measured time interval during discharge of said output capacitor through said precision resistor and multiplying said ratio by said known resistance of said precision resistor to provide a measurement of the impedance of said lead.

2. In an apparatus for stimulating body tissue comprising a pulse generator for generating stimulation pulses, including an output capacitor, a lead coupled to said pulse generator for delivering said stimulation pulses to body tissue and means within said pulse generator for measuring the impedance of said lead, the improvement wherein said impedance measuring means comprises:
   means for charging said output capacitor to a first voltage;
   means for defining a second voltage, less than said first voltage;
   a precision resistor of known resistance;
   means for discharging said output capacitor through said precision resistor;
   means for measuring the time interval during discharge of said output capacitor, from said first voltage to said second voltage, through said precision resistor;
   means for discharging said capacitor into said lead;
   means for measuring the time interval during discharge of said capacitor from said first voltage to said second voltage, through said lead; and
   means for deriving a measurement of the impedance of said lead as a function of said measured time intervals during discharge of said capacitor through said precision resistor and through said lead.

3. An apparatus according to claim 2 wherein said deriving means comprises means for determining the ratio of said measured time interval during discharge of said output capacitor through said lead to said measured time interval during discharge of said capacitor through said precision resistor and for multiplying said determined ratio by said known resistance of said precision resistor to provide said measurement of said lead impedance.

* * * * *

UNITED STATES PATENT AND TRADEMARK OFFICE
CERTIFICATE OF CORRECTION

PATENT NO. : 5,201,865
DATED : April 13, 1993
INVENTOR(S) : Kevin P. Kuehn

It is certified that error appears in the above-indentified patent and that said Letters Patent is hereby corrected as shown below:

Column 3, Line 65, delete "eges", and insert in its place --edges--.

Column 6, Line 42, delete "VDD2.", and insert in its place --VDD/2.--.

Column 8, Line 21, delete "FIG. 2.", and insert in its place --Figure 3.--.

Signed and Sealed this

Twenty-eight Day of February, 1995

*Attest:*

BRUCE LEHMAN

*Attesting Officer*     *Commissioner of Patents and Trademarks*